United States Patent [19]

Garner

[11] Patent Number: 5,166,743
[45] Date of Patent: Nov. 24, 1992

[54] ASSEMBLY FOR CONVERTING A SPECTROPHOTOMETER TO A FLUOROMETER

[75] Inventor: Harold R. Garner, Encinitas, Calif.
[73] Assignee: General Atomics, San Diego, Calif.
[21] Appl. No.: 746,855
[22] Filed: Aug. 19, 1991

Related U.S. Application Data

[63] Continuation-in-part of Ser. No. 407,539, Sep. 15, 1989, Pat. No. 5,092,674, which is a continuation-in-part of Ser. No. 377,476, Jul. 19, 1989, Pat. No. 4,991,958.

[51] Int. Cl.$^5$ .......................................... G01N 21/64
[52] U.S. Cl. .................................. 356/73; 250/458.1; 356/244; 356/318
[58] Field of Search ................. 356/317, 318, 244, 73; 250/458.1, 459.1, 461.1

[56] References Cited

U.S. PATENT DOCUMENTS

| | | | |
|---|---|---|---|
| 3,849,654 | 11/1974 | Malvin | 356/301 X |
| 3,877,817 | 4/1975 | Ralston | 356/180 |
| 4,006,990 | 2/1977 | Munk | 356/246 |
| 4,088,407 | 5/1978 | Schoeffel et al. | 356/317 |
| 4,440,497 | 4/1984 | Carey et al. | 356/246 |
| 4,935,875 | 6/1990 | Shah et al. | 364/497 |
| 4,991,958 | 2/1991 | Garner | 356/244 |

OTHER PUBLICATIONS

Garland "A Spectrophotometer and Fluorimeter for University Courses in Biochemical and Related Sciences" American Laboratory, vol. 8#11, Nov. 1976, pp. 57–62.

Primary Examiner—Vincent P. McGraw
Attorney, Agent, or Firm—Nydegger & Associates

[57] ABSTRACT

A conversion assembly for converting a spectrophotometer to a fluorometer which utilizes the light source and light detector of the spectrophotometer. The assembly has a conversion adaptor which is positionable in the spectrophotometer between the light source and the light detector. The adaptor is an enclosure having a receptacle for holding a sample container filled with the sample being analyzed and having openings formed therein to provide a light path for excitation light from the light source to the sample container and further to provide a light path for emitted luminescent light from the sample container to the light detector. In one embodiment the excitation light is centered on an optical shield on the front of the enclosure while light receiving openings at the edges of the front of the enclosure are positioned to receive off center excitation light. In another embodiment a light receiving opening is formed in the side of the enclosure and excitation light centered on the front of the enclosure is reflected around to the opening in the side of the enclosure by a plurality of reflectors.

4 Claims, 4 Drawing Sheets

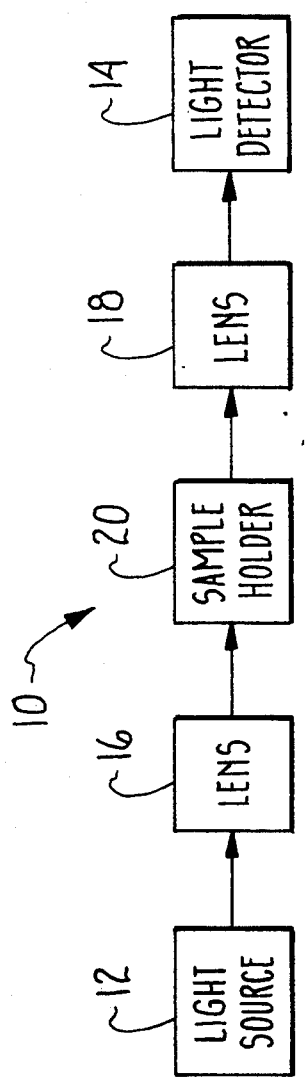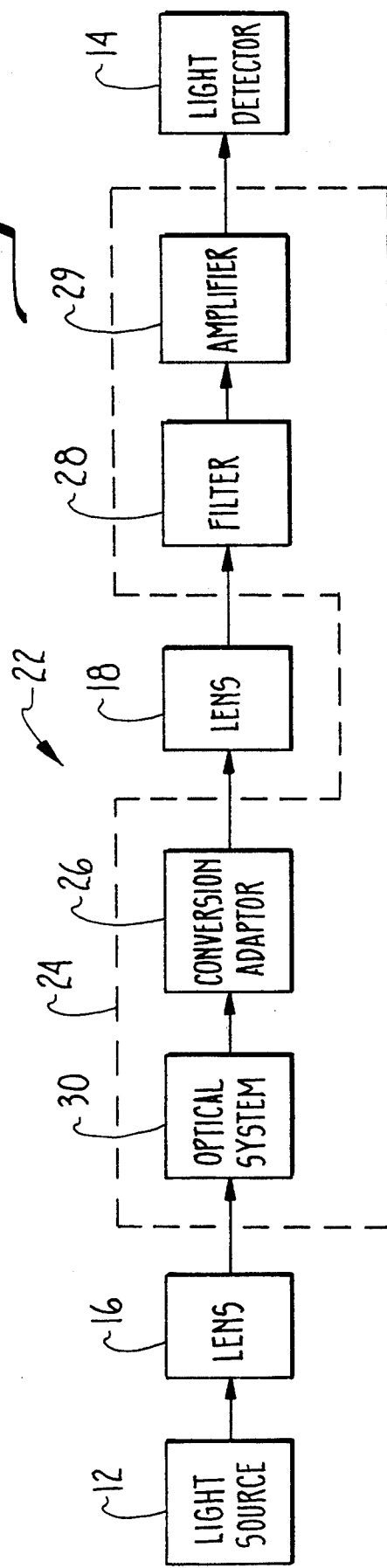

ASSEMBLY FOR CONVERTING A SPECTROPHOTOMETER TO A FLUOROMETER

This application is a continuation-in-part of my prior copending application "Micropipette Adaptor for Spectrophotometers with Temperature Control," Ser. No. 407,539 filed on Sep. 15, 1989, U.S. Pat. No. 5,092,674, which is a continuation-in-part application of my prior patent application for "Micropipette Adaptor for Spectrophotometers," Ser. No. 377,476, filed On Jul. 10, 1989, and issued as U.S. Pat. No. 4,991,958 on Feb. 12, 1991.

FIELD OF THE INVENTION

The device of the present invention pertains generally to diagnostic equipment. More particularly, the present invention pertains to devices which modify diagnostic equipment to interchangeably accomplish material quantization by alternative optical diagnostic techniques. The present invention is particularly, but not exclusively, useful for converting a spectrophotometer to a fluorometer.

BACKGROUND OF THE INVENTION

The quantization of a particular material is diagnostically useful in such diverse fields of technology as biology, chemistry and materials science. In particular, two of the more well known techniques for material quantization are spectrophotometry and fluorometry. It happens, however, that while both spectrophotometry and fluorometry involve procedures for the determination of specific optical characteristics of a material to be quantified, the phenomena observed by these procedures are significantly different.

In spectrophotometry, a beam of light is directed toward a sample of the material to be quantified, and the amount of light absorbed by this material at various light wavelengths as the light beam passes through it is measured to quantify the material. The spectrophotometer required to perform this technique typically includes very sensitive optical elements and is, consequently, quite expensive.

Fluorometry, in contrast to spectrophotometry, is based on the phenomenon whereby a material emits light of a characteristic wavelength when it is properly excited. Specifically, in fluorometry, molecules of a sample material are excited by absorbed light having a relatively short wavelength and, in response to this excitation, the molecules emit light at a relatively longer wavelength. Additionally, because of the basic differences in the underlying phenomena, fluorometers differ significantly from spectrophotometers. This is so in large part because a fluorometer must account for certain considerations which are not encountered during spectrophotometry. For instance, a fluorometer must be able to clearly differentiate the light which is emitted as fluorescence by the sample material from the light which is used to excite the material into its fluorescence. Further, the detecting elements of a fluorometer must have greater sensitivity than those used in a spectrophotometer in order to effectively sense the lower levels of light which typically result from fluorometry.

On the other hand, fluorometers and spectrophotometers do have some commonalities. Importantly, many components used in spectrophotometers are also used in fluorometers. Also, and not surprisingly, spectrophotometers and fluorometers can both be quite expensive to manufacture and maintain.

In view of the above, it is an object of the present invention to provide a spectrophotometer to fluorometer converter which effectively employs common components of a spectrophotometer in a resulting fluorometer. Another object of the present invention is to provide a spectrophotometer to fluorometer converter which is relatively inexpensive to produce. Still another object of the present invention is to provide a spectrophotometer to fluorometer converter which is relatively easy to manufacture and comparatively cost-effective to operate.

SUMMARY OF THE INVENTION

The present invention is a conversion assembly for converting a spectrophotometer to a fluorometer which utilizes the light source and light detector of the spectrophotometer. The assembly of the invention comprises a conversion adaptor which is positionable in the spectrophotometer between the light source and the light detector and enables the spectrophotometer to function as a fluorometer. The adaptor is an enclosure having a receptacle for holding a container filled with the sample being analyzed. The adaptor has openings formed therein to provide a light path for excitation light from the light source to the sample container and further to provide a light path for emitted light from the sample container to the light detector.

According to one embodiment, the adaptor has the configuration of a corner cube. A single excitation light inlet opening is provided through the front wall of the cube into the enclosure and is positioned somewhat off center of direct alignment between the light source and the sample container. The portion of the front wall which is in direct alignment with the light source and the sample container, has an optical shield integral therewith which substantially blocks the transmission of light therethruugh.

The back wall of the corner cube has three faces including a center face which is substantially parallel to the front wall and two end faces on either side of the center face which are at obtuse angles to the center face, thereby providing a concave surface on the back wall. Both end faces are light reflective and are positioned lateral to the sample container on opposite sides thereof. One of the end faces is in direct alignment with the inlet opening to receive excitation light therethrough from the light source. The angular orientation of this end face is such that light so received is reflected onto the sample container. The opposite end face is oriented at an angle to receive reflected light passing through the sample container and reflect it back to the front wall of the cube where the light is absorbed on the backside of the optical shield.

The back wall of the corner cube is further provided with an outlet opening positioned to receive light emitted from the sample container. The opening is in direct alignment with the sample container and the light source. A lens may be provided across the outlet opening which is capable of focusing the emitted light passing to the detector.

According to a second embodiment of the present invention, the conversion adaptor is provided with two excitation light inlet openings through the front wall of the cube into the enclosure which are positioned at opposite sides of the front wall and are somewhat off center of direct alignment between the light source and the sample container. An optical shield is provided over the portion of the front the sample container. The optical shield is integral with the front wall and substantially blocks the transmission of light therethrough. Each inlet opening is aligned with a respective end face on the back wall of the cube to provide two separate light pathways between the light source and sample container via the inlet openings and end faces respectively. In all other respects, the conversion adaptors of the first two embodiments are substantially the same.

In a third embodiment of the present invention, the conversion adaptor is an enclosure having a regular cubic configuration. A single excitation light inlet opening is provided through the side wall of the cube at a position lateral to the sample container which is capable of receiving light from the light source and disposing it onto the sample container. The front wall, which is in direct alignment with the light source and the sample container, is opaque and substantially blocks transmission of light therethrough. The back wall of the cube is a substantially straight and flat nonreflective surface. The back wall is provided with an outlet opening positioned to receive light emitted from the sample container and is in direct alignment with the sample container and the light source. As with the first two embodiments, a lens may be provided across the outlet opening which is capable of focusing the emitted light passing to the detector.

The assembly of the third embodiment further includes an optical system comprising a plurality of light reflectors positioned between the adaptor and the light source which are aligned to direct light from the light source into the adaptor enclosure via the lateral inlet opening. Specifically, a first light reflector is provided in alignment with the light source and adaptor. A second light reflector is disposed laterally away from the first reflector and the adaptor. Finally, a third light reflector is provided in alignment with the second reflector and adjacent the inlet opening of the adaptor.

In accordance with all three embodiments set forth above, the conversion assembly of the present invention may further comprise a monochrometer or filter positioned between the conversion adaptor and detector which only allows certain predetermined wavelengths of emitted light from the sample container to pass through to the light detector. The predetermined wavelengths allowed through the filter or monochrometer correspond to those wavelengths which are detectable by the detector and which are characteristic of luminescent light emissions caused by the particular excitation light wavelength.

Finally, the conversion assembly may include a light amplifier positioned between the light detector and the monochrometer or filter which further processes those wavelengths of emitted light passing through the monochrometer or filter to the detector. The processed light discharged by the amplifier to the detector is of a quality which enables the detector to operate at a required level of sensitivity.

In operation, the assembly is placed in the fluorometer and a sample container filled with the sample material to be fluorometrically analyzed is inserted into its receptacle in the adaptor. The light source is activated to direct light toward the adaptor and the light enters the inlet opening or openings of the adaptor which direct the light onto the container containing the sample material in a direction substantially perpendicular to the alignment of the light source and the container. Some of the directed light is absorbed by the sample which excites the sample causing it to emit luminescent light. The emitted light which is at a different wavelength from the excitation light is transmitted in a direction normal to the excitation light out of the adaptor enclosure and through the lens of the outlet opening to the filter or monochrometer. The light passing therethrough continues on to the amplifier and finally to the detector which characterizes the emitted light received for quantitatively analyzing the sample material.

The assembly of the present invention is particularly advantageous because it enables conversion of a spectrophotometer to a fluorometer with the insertion of relatively few additional components. Most of the components of the spectrophotometer are utilized by the fluorometer after conversion and the bulk of those components which must be added to effect conversion are integrated into the adaptor which simplifies the conversion procedure and further enables easy reconversion of the fluorometer back to a spectrophotometer if desired.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a schematic diagram of a conventional spectrophotometer;

FIG. 2 is a schematic diagram showing cooperative engagement of the conversion assembly of the present invention with a spectrophotometer to create a fluorometer;

DESCRIPTION OF PREFERRED EMBODIMENTS

Figure 3:
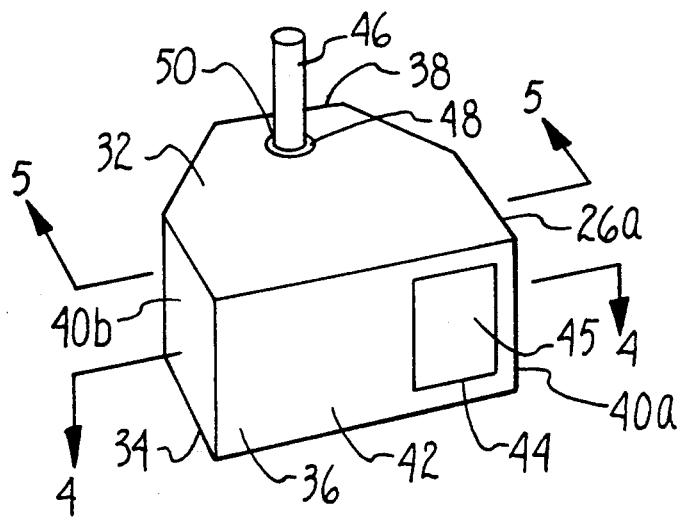
FIG. 3 is a perspective of a conversion adaptor employed in the conversion assembly of the present invention.

Referring initially to FIG. 1, the primary functional components of a conventional spectrophotometer designated generally as 10 are shown including a light source 12 and a light detector 14 as well as intervening lenses 16, 18 and a sample holder 20 which is typically a cuvette. The components are shown connected by directional arrows which represent light pathways. FIG. 2 shows a fluorometer designated generally as 22 resulting from the conversion of spectrophotometer 10 using the conversion assembly of the present invention which is designated by dashed box 24. The conversion assembly 24 comprises a conversion adaptor 26, a monochrometer or filter 28, and an amplifier 29. According to one embodiment of the invention, an optical system designated by dashed box 30 may also be provided as a component of the conversion assembly 24.

As is apparent from a comparison of FIGS. 1 and 22 conversion of the spectrophotometer 10 to the fluorometer 2, is accomplished simply by removal of sample holder 20, and if desired lenses 16, 18, from spectrophotometer 10 and placement of conversion assembly 24 therein. The resulting fluorometer 22 utilizes light source 12 and light detector 14 of the spectrophotometer 10. The present invention is particularly suited to the conversion of a spectrophotometer wherein the lenses 16, 18 and sample holder 20 are integrated into a single unit such as disclosed in U.S. Pat. No. 4,991,958 to the present inventor, which is incorporated herein by reference. The integrated unit facilitates the speed and ease of the conversion procedure. It is noted in FIG. 2 that conversion adaptor 26 is positioned between light source 12 and light detector 14 in the position formally occupied by sample holder 20 of spectrophotometer 10. However, unlike spectrophotometer 10 wherein the light from light source 12 is received by the sample centered directly thereon, in fluorometer 22 the light from light source 12 is received by the sample off center therefrom.

FIG. 3 shows a conversion adaptor 26a as used in a first embodiment of the present invention. Adaptor 26a has the configuration of a corner cube having a top wall 32, a bottom wall 34, a front wall 36, a partitioned back wall 38, and side walls 40a, 40b which in sum form an enclosure 42. An excitation light inlet opening 44 is provided through front wall 36 into the interior 45 of enclosure 42 and is aligned to one side of front wall 36 slightly off center from light directed at adaptor 26a by light source 12 as will be shown with reference to FIG. 4. A transparent container 46, which contains the sample material being analyzed, is positioned in interior 45 through circular aperture 48 in top wall 32. As shown herein, sample container 46 is a micropipette, but it is understood that within the scope of the present invention sample container 46 may be a cuvette, having dimensions considerably larger than a micropipette, or any other type of sample container known to one skilled in the art. An annular seal 50 in the form of a bushing is provided in aperture 48 to secure and align sample container 46 therein. Front wall 36 excluding inlet opening 44 has an optical shield 52 integral therewith which substantially blocks the transmission of light therethrough.

Figure 4:
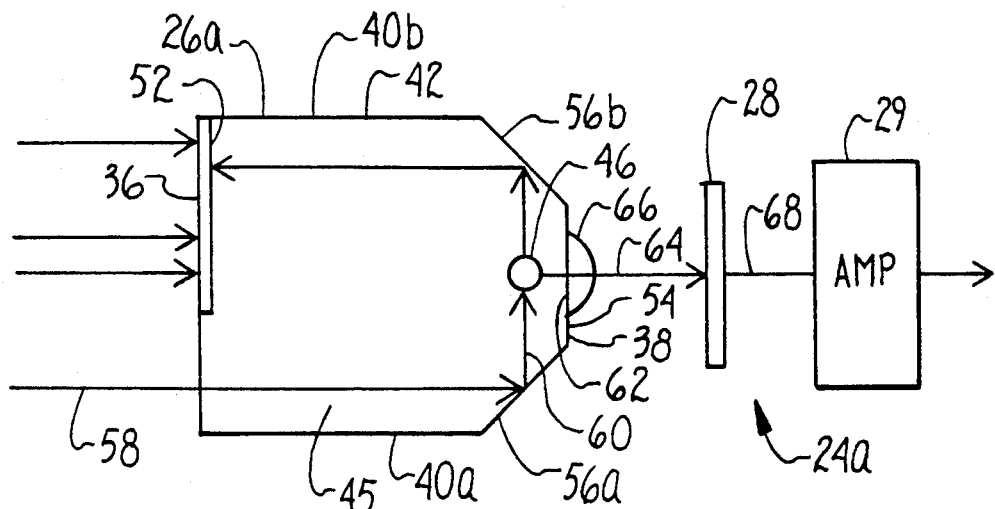
FIG. 4 is a cross-section of the adaptor as seen along line 4—4 in FIG. 3 in cooperation with other components of the conversion assembly shown schematically.

The detail of interior 45 is best seen with reference to FIG. 4. Back wall 38 is partitioned into three faces including a center face 54 which is substantially parallel to front wall 36 and end faces 56a, 56b on either side of center face 54 which are at obtuse angles $\phi_1$ and $\phi_2$ to center face 54. End faces 56a, 56b are light reflective and are positioned lateral to sample container 46 on opposite sides thereof. End face 56a is in direct alignment with inlet opening 44 to receive excitation light 58 therethrough from light source 12. Angles $\phi_1$ and $\phi_2$ are preferably about 135° each, such that light 58 received by end face 56a is reflected onto sample container 46 and reflected light 60 passing through sample container 46 is reflected back to front wall 36 to be absorbed by optical shield 52. Back wall 38, and more specifically center face 54, has an outlet opening 62 formed therein which is positioned to receive light 64 emitted from sample container 46 at a substantially normal angle to reflected light 60. A directing lens 66 may be provided across the outlet opening 62 which is capable of focusing emitted light 64 exiting adaptor 26a. Conversion assembly 24a of the first embodiment further comprises light processing means 28 and 29. Means 28 is a monochrometer or a filter positioned between conversion adaptor 26a and light detector 14 which only allows certain predetermined wavelengths of filtered light 68 to pass through. Light processing means 29 is an amplifying means such as a microchannel plate or a detector-/amplifier light emitting diode which amplifies the filtered light 68 sent to light detector 14.

Figure 5:
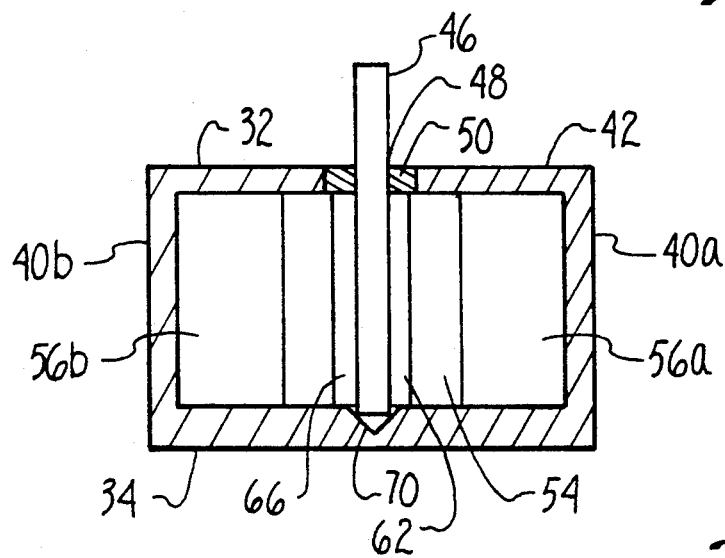
FIG. 5 is a cross-section of the adaptor as seen along line 5—5 in FIG. 3.

FIG. 5 shows sample container 46 held in interior 45 by means of bushing 50 at the upper end of sample container 46. The lower end of sample container 46 is secured by placement into a conical well 70 formed in the bottom wall 34 of adaptor 26a. The adaptor enclosure 42 is preferably fabricated from a rigid material such as black delrin plastic. Lens 66 can be adjustably mounted across outlet opening 62 by screws or snap-in attachment in a manner known to one skilled in the art. Lens 66 is preferably in the shape of a half cylinder and may be fabricated from substantially any appropriate light transmitting material including quartz, glass, sapphire, and fused silicon.

Figure 6:
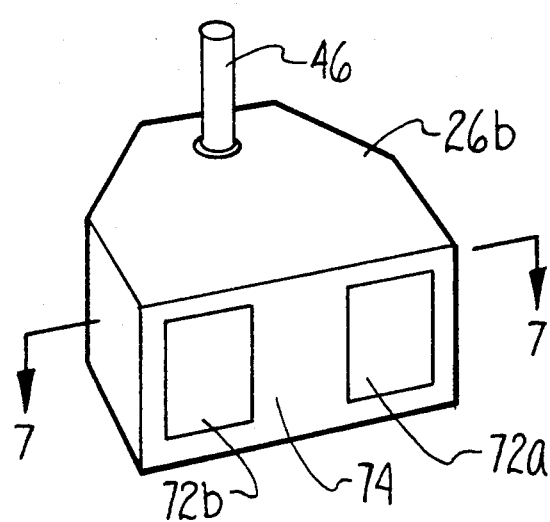
FIG. 6 is a perspective of a second embodiment of a conversion adaptor employed in the conversion assembly of the present invention.
Figure 7:
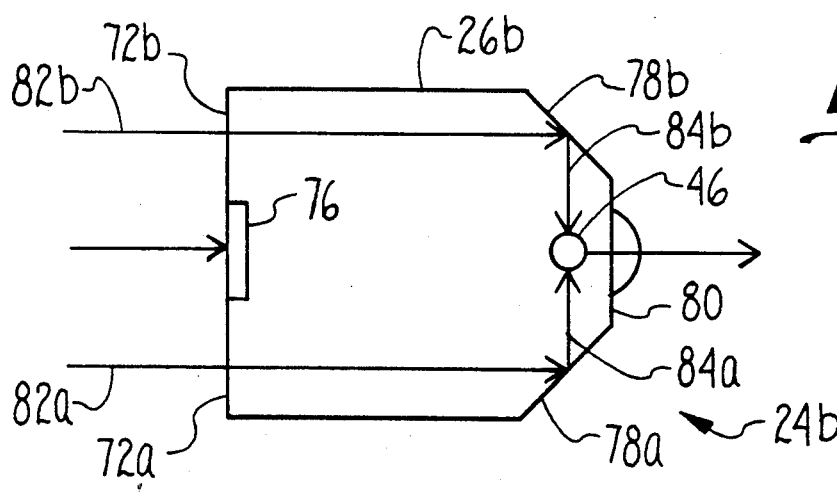
FIG. 7 is a cross-section of the adaptor as seen along line 7—7 in FIG. 6 in cooperation with other components of the conversion assembly shown schematically.

FIG. 6 shows another corner cube conversion adaptor 26b for use in a second embodiment of the present invention. Conversion adaptor 26b has two excitation light inlet openings 72a, 72b through front wall 74 at opposite sides thereof. Front wall 74 has an optical shield 76 integral therewith which is just wide enough to block the excitation light from directly illuminating the sample. As shown in FIG. 7, inlet openings 72a, 72b are aligned with end faces 78a, 78b on back wall 80 of adaptor 26b to receive off center excitation light 82a, 82b into adaptor 26b on two separate pathways such that light 82a, 82b reaches sample container 46 as reflected light 84a, 84b respectively. In all other respects, assembly 24b, and assembly 24a of FIG. 4 are substantially the same.

Figure 8:
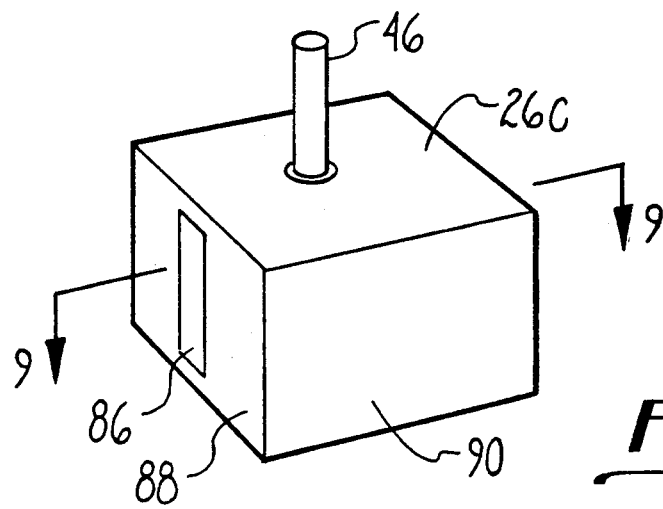
FIG. 8 is a perspective of a third embodiment of a conversion adaptor employed in the conversion assembly of the present invention.
Figure 9:
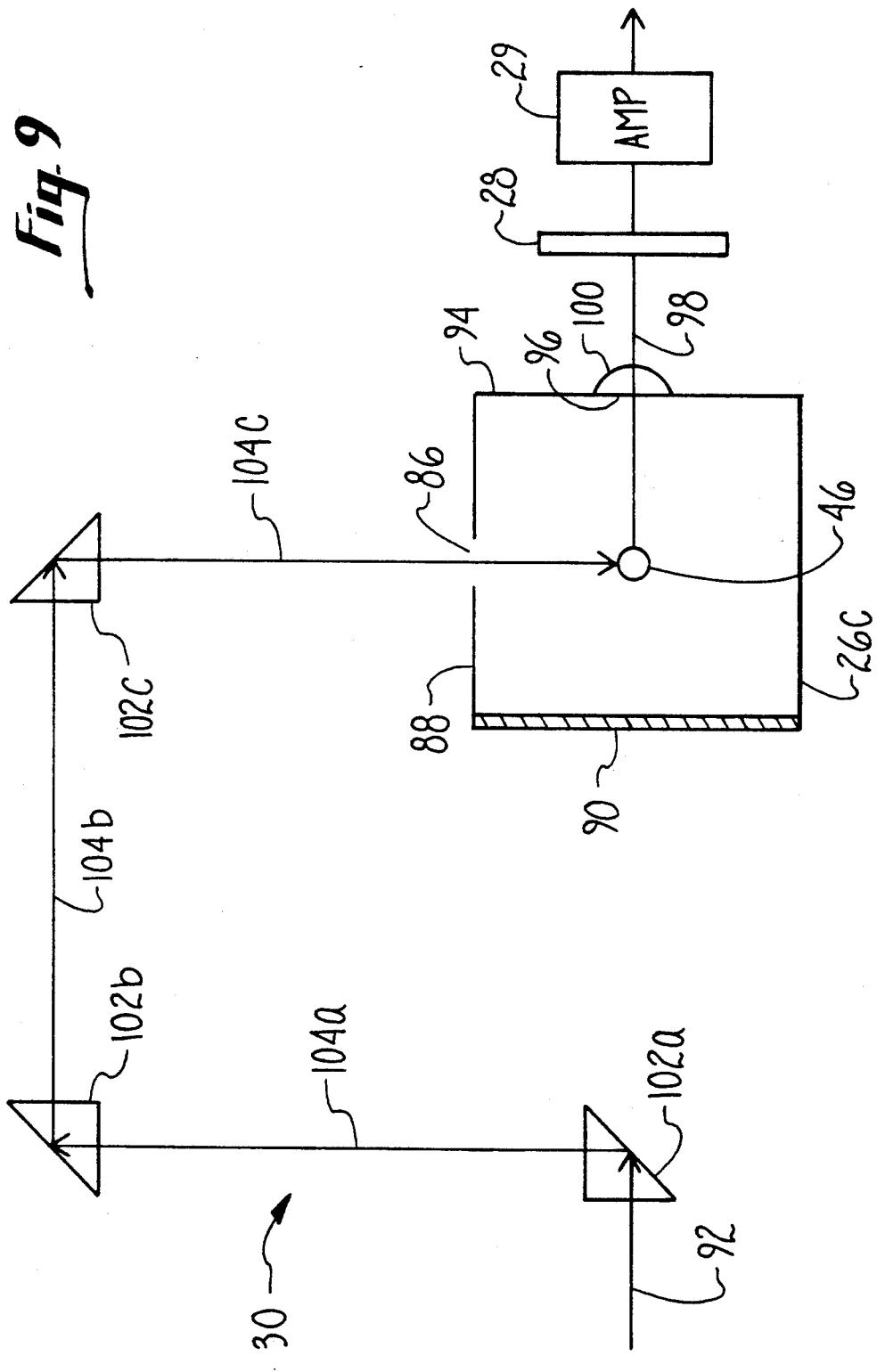
FIG. 9 is a cross-section of the adaptor as seen along line 9—9 in FIG. 8 in cooperation with other components of the conversion assembly shown schematically.

FIG. 8 shows a conversion adaptor 26c in the shape of a conventional cube for use in a third embodiment of the present invention. Adaptor 26c has a single excitation light inlet opening 86 through a side wall 88 of adaptor 26c at a position lateral to sample container 46 which is maintained in adaptor 26c in substantially the same manner as shown in FIG. 5. Referring to FIG. 9, front wall 90 is in direct alignment with excitation light 92 from light source 12 and is opaque to substantially block transmission of light therethrough. Back wall 94 is a substantially planar nonreflective surface and has an outlet opening 96 positioned to receive light 98 emitted from sample container 46 in the manner of the first two embodiments. Likewise, a lens 100 may be provided across outlet opening 96 and the assembly 24c is provided with a filter or monochrometer 28 and amplifier 29.

Assembly 24c of this embodiment further includes optical system 30 comprising three light reflectors 102a, 102b, 102c which may be prisms, mirrors, or the like. As shown here, prisms 102a, 102b, 102c are positioned between adaptor 26c and light source 12 which are aligned to direct excitation light 92 into inlet opening 86. Specifically, first reflective prism 102a is directly aligned with light 92 from light source 12 and sample container 46. Second reflective prism 102b is disposed laterally away from first prism 102a and adaptor 26c to receive reflected light 104a from first prism 102a to the front and side of adaptor 26c. Third prism 102c is aligned with second prism 102b adjacent inlet opening 86 to receive reflected light 104b from prism 102b and reflect it through inlet opening 86 as reflected light 104c to sample container 46.

In operation, conversion of a spectrophotometer 10 as shown in FIG. 1 is effected by removing sample holder 20. Lenses 16, 18 may or may not be removed as desired. In any case, sample holder 20 is replaced with the conversion assembly 24 of FIG. 2. Referring to FIGS. 3-5, a sample container 46 is filled with a sample material to be fluorometrically analyzed and inserted into enclosure 42 of adaptor 26a through aperture 48. Light source 12 is activated to direct excitation light 58 onto front wall 36 aligned therewith. Light 58 centered on front wall 36 is blocked from contacting sample container 46 directly by optical shield 52, but the off center portion of excitation light 58 enters enclosure 42 through inlet opening 44.

Light 58 entering inlet opening 44 strikes end face 56a and is reflected onto sample container 46 containing the sample material along a pathway 60 substantially perpendicular to excitation light pathway 58. The sample material absorbs a portion of light 60, thereby exciting the sample and causing it to emit luminescent light 64 in a normal direction to reflected light 60. Emitted light 64 exits enclosure 42 through lens 66 across outlet opening 62 which focuses it onto filter or monochrometer 28. Resulting filtered light 68 passes therethrough to amplifier 29 for amplification and continues on to detector 14 for ultimate analysis. Reflected light 60 not absorbed by the sample material passes therethrough, striking end face 56b and reflecting onto the backside of optical shield 52 where it is absorbed.

It is appreciated that in operation the embodiment of the present invention described above uses the off center portion of centered light from light source 12 of spectrophotometer 10 to enable fluorometric analysis of a sample material. By providing a conversion assembly which properly directs the off center light onto the sample material, analysis of the emitted light can be performed without interference from the excitation light.

The conversion assembly 24b of the second embodiment shown in FIGS. 6 and 7 operates in substantially the same manner as the first embodiment except that off center excitation light 82a, 82b is received through inlet openings 72a, 72b on both sides of front wall 74. Accordingly, reflected light 84a, 84b is directed onto sample container 46 from opposite sides thereof to double the level of excitation for generation of luminescent light.

Finally, with reference to FIGS. 8 and 9, the third embodiment operates by using optical system 30 to divert centered excitation light 92 away from front wall 90 and direct reflected light 104a, 104b, 104c to the side of adaptor 26c where it is received in inlet opening 86. Thereafter, conversion assembly operates in substantially the same manner as the first two embodiments.

While the particular Assembly for Converting a Spectrophotometer to a Fluorometer as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

I claim:

1. A conversion assembly for converting a spectrophotometer having a light source and a light detector to a fluorometer utilizing said light source to generate excitation light and said light detector to analyze emitted luminescent light, said conversion assembly comprising:

a conversion adaptor defining an enclosure having means formed therein for retaining a sample container fillable with a sample to be fluorometrically analyzed, said adaptor positionable in a centered path of said excitation light;

an inlet opening in said adaptor laterally positioned relative to said sample container and said centered path of said excitation light to receive reflected excitation light from said light source;

means for reflecting light from said light source into said inlet opening and onto said sample container comprising a plurality of light reflectors including a first reflector positioned in said centered path of said excitation light, a second reflector laterally positioned relative to said first reflector and in light communication therewith, and a third reflector laterally positioned relative to said inlet opening and in light communication with said second reflector and said sample container to dispose reflected light onto said sample container; and an outlet opening in said adaptor positioned to receive said emitted luminescent light from said sample container and aligned to direct said emitted luminescent light to said light detector.

2. A conversion assembly for converting a spectrophotometer as recited in claim 1, further comprising means for selectively permitting only a predetermined wavelength of said emitted luminescent light from said sample container to reach said light detector.

3. A conversion assembly for converting a spectrophotometer as recited in claim 1 wherein said plurality of light reflectors are a plurality of light reflective prisms.

4. A conversion assembly for converting a spectrophotometer as recited in claim 1 wherein said outlet opening receives said emitted luminescent light substantially normal to said reflected light.

* * * * *